(12) United States Patent
Kerbel

(10) Patent No.: US 7,740,841 B1
(45) Date of Patent: Jun. 22, 2010

(54) THERAPEUTIC METHOD FOR REDUCING ANGIOGENESIS

(75) Inventor: Robert Kerbel, Toronto (CA)

(73) Assignee: Sunnybrook Health Science Center, Ontario (CA)

( * ) Notice: Subject to any disclaimer, the term of this patent is extended or adjusted under 35 U.S.C. 154(b) by 0 days.

(21) Appl. No.: 09/539,692

(22) Filed: Mar. 31, 2000

Related U.S. Application Data

(60) Provisional application No. 60/178,791, filed on Jan. 28, 2000.

(51) Int. Cl.
  *A61K 39/395* (2006.01)
  *A61K 39/00* (2006.01)
  *C12P 21/08* (2006.01)
  *C07K 16/28* (2006.01)

(52) U.S. Cl. ............. 424/130.1; 424/141.1; 424/142.1; 424/143.1

(58) Field of Classification Search ............... 424/141.1, 424/145.1, 142.1, 143.1, 174
See application file for complete search history.

(56) References Cited

U.S. PATENT DOCUMENTS

| | | | |
|---|---|---|---|
| 4,853,221 A * | 8/1989 | Elslager et al. ............. 424/649 |
| 4,946,778 A | 8/1990 | Ladner et al. |
| 5,036,003 A | 7/1991 | Olander et al. |
| 5,190,198 A | 3/1993 | Cucheran |
| 5,190,918 A | 3/1993 | Cucheran |
| 5,192,744 A | 3/1993 | Bouck et al. |
| 5,200,397 A | 4/1993 | Deutch et al. |
| 5,399,667 A | 3/1995 | Frazier et al. |
| 5,399,677 A | 3/1995 | Wolfman et al. |
| 5,506,208 A | 4/1996 | Eyal et al. |
| 5,648,461 A | 7/1997 | Eval et al. |
| 5,652,109 A | 7/1997 | Kim et al. |
| 5,652,110 A | 7/1997 | Kim et al. |
| 5,654,277 A | 8/1997 | Eyal et al. |
| 5,659,013 A | 8/1997 | Senger et al. |
| 5,660,827 A | 8/1997 | Thorpe et al. |
| 5,684,461 A | 11/1997 | Jones |
| 5,696,131 A * | 12/1997 | Baguley et al. ............. 514/297 |
| 5,696,153 A * | 12/1997 | Ainsworth et al. .......... 514/449 |
| 5,730,977 A | 3/1998 | Ooka et al. |
| 5,753,230 A | 5/1998 | Brooks et al. |
| 5,759,996 A | 6/1998 | Cheng et al. |
| 5,767,071 A | 6/1998 | Palladino et al. |
| 5,770,195 A * | 6/1998 | Hudziak et al. |
| 5,770,563 A | 6/1998 | Roberts et al. |
| 5,773,412 A | 6/1998 | Cheng et al. |
| 5,780,426 A | 7/1998 | Palladino et al. |
| 5,840,301 A | 11/1998 | Rockwell et al. |
| 5,840,692 A | 11/1998 | Deutch et al. |
| 5,855,866 A | 1/1999 | Thorpe et al. |
| 5,861,499 A | 1/1999 | Rockwell et al. |
| 5,874,542 A | 2/1999 | Rockwell et al. |
| 5,877,289 A | 3/1999 | Thorpe et al. |
| 5,919,792 A | 7/1999 | Duggan et al. |
| 5,952,341 A | 9/1999 | Duggan et al. |
| 5,955,311 A | 9/1999 | Rockwell et al. |
| 5,965,132 A | 10/1999 | Thorpe et al. |
| 5,981,546 A | 11/1999 | Duggan et al. |
| 6,004,555 A | 12/1999 | Thorpe et al. |
| 6,017,925 A | 1/2000 | Duggan |
| 6,017,926 A | 1/2000 | Askew et al. |
| 6,100,254 A * | 8/2000 | Budde et al. ............... 514/221 |
| 6,302,838 B1 * | 10/2001 | O'Reilly et al. ............. 514/365 |
| 6,342,219 B1 * | 1/2002 | Thorpe et al. ............. 424/145.1 |
| 6,824,777 B1 * | 11/2004 | Alitalo et al. ............. 424/143.1 |
| 6,884,879 B1 * | 4/2005 | Baca et al. ............... 536/23.53 |

FOREIGN PATENT DOCUMENTS

| | | |
|---|---|---|
| EP | 0 239 400 A2 | 3/1987 |
| EP | 0 239 400 A3 | 3/1987 |
| EP | 0 332 424 A2 | 3/1989 |
| EP | 0 332 424 A3 | 3/1989 |
| EP | 0 338 745 A1 | 4/1989 |
| EP | 0 506 477 A1 | 3/1992 |
| WO | WO 89/09622 | 10/1989 |
| WO | WO 92/14748 | 9/1992 |
| WO | WO 93/21319 | 10/1993 |
| WO | WO 9521868 * | 8/1995 |

(Continued)

OTHER PUBLICATIONS

Lokieh et al., Am J Clinical Oncology 7(5): 551-3, Oct. 1984.*

(Continued)

*Primary Examiner*—Phuong Huynh
(74) *Attorney, Agent, or Firm*—Lucas & Mercanti, LLP

(57) ABSTRACT

A method of controlling or treating an angiogenic dependent condition in a mammal, preferably in a human by administering an anti-angiogenic molecule such as an angiogenesis growth factor antagonist, and a chemotherapeutic agent in amounts and frequencies effective, in combination, to produce a regression or arrest of said condition while minimizing or preventing significant toxicity of the chemotherapeutic agent. Also a kit for controlling or treating an angiogenic dependent condition in a mammal, preferably in a human, comprising an anti-angiogenic molecule, such as an angiogenesis growth factor antagonist, and a chemotherapeutic agent in amounts effective, in combination, to produce a regression or arrest of said condition while minimizing or preventing significant toxicity of the chemotherapeutic agent.

5 Claims, 2 Drawing Sheets

FOREIGN PATENT DOCUMENTS

| WO | WO 97/05250 A2 | 2/1997 |
| WO | WO 97/05250 A3 | 2/1997 |
| WO | WO 98/33917 | 8/1998 |
| WO | WO 99/16465 | 4/1999 |
| WO | WO 00/34337 | 6/2000 |
| WO | WO 00/51686 | 9/2000 |
| WO | WO 00/69459 | 11/2000 |

OTHER PUBLICATIONS

Jackson et al., Cancer chemotherapy and pharmacology 10(3): 217-20, 1983.*
Obrist et al., Cancer chemotherapy and pharmacology 2(4): 233-37, 1979.*
Klement et al., J Clinical Investigation 105(8): R15-R23, Apr. 2000.*
Stryer et al, in Biochemistry, Third edition, W H Freeman Company, New York, pp. 31-33, 1998.*
Ngo et al, 1994, The Protein Folding Problem and Tertiary Structure Prediction, pp. 492-495.*
Abaza et al, J of Protein Chemistry 11(5): 433-444, 1992.*
Fogarty et al, The Scientist 16(16): 33, Mar. 2002.*
Jakobovits et al, Advanced Drug Delivery Reviews 31: 33-42, 1998.*
Glade-Bender et al, Exp Opinion Biol Ther 3(2): 263-276, 2003.*
Witte et al, Cancer Metastasis Rev 17(2): 155-61, Jun. 1998.*
Baca et al, J Biol Chem 272(16): 10678-10684, 1997.*
Folkman et al, Forum 9(3): 59-223, 1999.*
Vassal et al, Int J Cancer 73: 156-163, 1997.*
Teicher et al, Breast Cancer Research and Treatment 36: 227-236, 1995.*
Weitman et al, J Clinical Oncology 11(5): 820-821, May 1993.*
N. Takahashi et al., "Antiangiogenic Therapy of Established Tumors in Human Skin/Severe Combined Immunodeficiency Mouse Chimeras by Anti-Endoglin (CD105) Monoclonal Antibodies, and Synergy between Anti-Endoglin Antibody and Cyclophosphamide" Cancer Research 61, Nov. 1, 2001, pp. 7846-7854.
L. Bello et al., "Low-dose Chemotherapy Combined with an Antiangiogenic Drug Reduces Human Glioma Growth in Vivo", Cancer Research 61, Oct. 15, 2001, pp. 7501-7506.
G. Klement et al., "Differences in Therapeutic Indexes of Combination Metronomic Chemotherapy and an Anti-VEGFR-2 Antibody in Multidrug-resistant Human Breast Cancer Xenografts", Clinical Cancer Research, vol. 8, Jan. 2002, pp. 221-232.
L. Zhang et al., "Combined Anti-Fetal Liver Kinase 1 Monoclonal Antibody and Continuous Low-Dose Doxorubicin Inhibits Angiogenesis and Growth of Human Soft Tissue Sarcoma Xenografts by Induction of Endothelial Cell Apoptosis", Cancer Research 62, Apr. 1, 2002, pp. 2034-2042.
Baringa, Angiogenesis Research: Cancer Drugs Found to Work in New Way, Science Apr. 14, 2000 (288) 5464 p. 245.
Fidler et al., Chemotherapeutic drugs—more really is not better, Nature Medicine May 2000 (6)5, pp. 500-502.
Hanahan et al., Less is more, regularly: metronomic dosing of cytotoxic drugs can target tumor angiogenesis in mice, J. Clin. Invest. Apr. 2000, 105(8), pp. 1045-1047.
Kamen et al., High-Time Chemotherapy or High Time for Low Dose, Journal of Clinical Oncology, Aug. 18, 2000 (16) pp. 2935-2937.
Breier et al., Development (Camb.) 114:521 (1992).
Klagsburn, M. and D'Amore, P. Annual Rev. Physiol. 53:217-239 (1991).
Kozbor et al., Immunology Today 4:72, (1983).
Database WPI, Section Ch, Week 199828 Derwent Publications Ltd., London, GB; An 1998-316701 XP002286349, May 6, 1998.
Tortora G et al., "Oral Administration of Chimeric MBO Antisense-Protein Kinase a Inhibits Growth, Angiogenesis and Growth Factors Production and Cooperates With Cytotoxic Drugs in Human Cancer Xenografts" European Journal of Cancer, Pergamon Press, Oxford, GB vol. 35, No. Suppl. 4, Sep. 1999, XP008004191.
Sola F. et al., "The antitumor efficacay of cytotoxic drugs is potentiated by treatment with PNU 145156E, a growth -factor-complexing molecule" Cancer Chemotherapy and Pharmacology, Springer Verlag, Berlin, DE, vol. 43, No. 9, pp. 241-246, 1999.

Yamaoka M. et al., "Angiogenesis Inhibitor TNP-470 (AGM-1470) Potently Inhibits the Tumor Growth of Hormone-Independent Human Breast and Prostate Carcinoma Cell Lines" Cancer Research, American Association for Cancer Research, Baltimore, MD, US, vol. 53, pp. 5233-5236, Nov. 1, 1993, XP001064890.
Kerbel R.S. et al. "Establishing a link between oncogenes and tumor angiogenesis" Molecular Medicine, Blackwell Science, Cambridge, MA, US vol. 4, No. 5, pp. 286-295, May 1, 1998, XP002089417.
Klement G. et al., "Continous Low-dose therapy with vinblastine and VEGF receptor-2 antibody induces sustained tumor regression iwthout overt toxicity" Journal of Clinical Investigation, New York, NY, US, vol. 105, No. 8, pp. R15-R24, Apr. 2000, XP002269717.
Kerbel R.S., et al., "'Accidental' Anti-angiogenic drugs: Anti-ONcogene directed signal transduction inhibitors and conventional chemotherapeutic agents as examples" European Journal of Cancer, vol. 36, No. 10, pp. 1248-1257, Jun. 2000, XP002286348.
Folkman, J. and Klagsbrun, M., Science, vol. 235, pp. 442-447, Jan. 1987, "Angiogenic Factors".
Brown, L. F. et al., J. Exp. Med, vol. 176, pp. 1375-1379, Nov. 1992, "Expression of Vascular Permeability Factor (Vascular Keratinocytes during Wound Healing".
Ferrara, N., Endocr. Rev., vol. 13, No. 1, pp. 18-32, Mar. 1992, "Molecular and Biological Properties of the Vascular Endothelial Growth Factor Family of Proteins".
Plate, H. K. et al., Nature, vol. 359, pp. 845-848, Oct. 1992, Vascular endothelial growth factor is a potential tumour angiogenesis factor in human gliomas in vivo.
Plate, K. et al., Cancer Res., vol. 53, No. 23, pp. 5822-5827, Dec. 1993, "Up-Regulation of Vascular Endothelial Growth Factor and its Cognate Receptors in a Rat Glioma Model of Tumor Angiogenesis".
Berkman, R. A. et al., J. Clin. Invest. vol. 91, pp. 153-159. Jan. 1993, "Expression of the Vascular premeability Factor/Vascular Endothelial Growth Factor Gene in Central Nervous System Neoplasms".
Shweiki, D. et al., Nature, vol. 359, No. 6398, pp. 843-845, Oct. 1992, "Vascular endothelial growth factor induced by hypoxia may mediate hypoxia-initiated angiogenesis".
Millauer, B. et al., Cell, vol. 72, pp. 835-846, (1993), "High Affinity VEGF Binging and Developmental Expression Suggest Flk-1 as a Major Regulator of Vasculogenesis and Angiogenesis".
Kaipainen, A. et al., J. Exp. Med., vol. 178, pp. 2077-2088, Dec. 1993, "The Related FLT4, FLT1, and KDR Receptor Tyrosine Kinases Show Distinct Expression Patterns in Human Fetal Endothelial Cells".
Terman, B. I. et al., Oncogene, vol. 6, No. 9, pp. 1677-1683, Sep. 1991, "Identification of a new endothelial cell growth factor receptor tyrosine kinase".
Kim, K. J. et al., Nature, vol. 362, No. 6423, pp. 841-844, Apr. 1993, "Inhibition of vascular endothelial growth factor-induced angiogenesis suppresses tumour growth in vivo".
Shibuya, M. et al., vol. 5, No. 4, pp. 519-524, Apr. 1990, "Nucleotide sequence and expression of a novel human receptor-type tyrosine kinase gene (flt) closely related to the fms family".
Matthews, W. et al., vol. 88, No. 20, pp. 9026-9030, Oct. 1991, "A receptor tyrosine kinase cDNA isolated from a population of enriched primitive hematopoietic cells and exhibiting close genetic linkage to c-kit".
Lin, P. et al., J. Clin. Invest., vol. 100, No. 8, pp. 2072-2078, Oct. 1997, "Inhibition of Tumor Angiogenesis Using a Soluble Receptor Establishes a Role for Tie2 in Pathologic Vascular Growth".
Benjamine, L. E. et al., The Journal of Clinical Investigation, vol. 103, No. 2, pp. 159-165, 1998 "Selective ablation of immature blood vessels in established human tumors follows vascular endothelial growth factor withdrawal".
Alon, T. et al., Nature Medicine, vol. 1, No. 10, pp. 1024-1028, Oct. 1995, "Vascular endothelial growth factor acts as a survival factor for newly formed retinal vessels and has implications for retinopathy of prematurity".
Jain, R. K. et al., Proc. Natl. Acad. Sci. USA, vol. 95, pp. 10820-10825, Sep. 1998, "Endothelial cell death, angiogenesis, and microvascular function after castration in an androgen-dependent tumor: Role of vascular endothelial growth factor".

Prewett, M. J. et al., Cancer Res., vol. 59, No. 20, pp. 5059-5402, Oct. 1999, "Antivascular Endothelial Growth Factor Receptor (Fetal Liver Kinase 1) Monoclonal Antibody Inhibits Tumor Angiogenesis and Growth of Several Mouse and Human Tumors".

Fong T. A. T. et al., Cancer Research, vol. 59, pp. 99-106, Jan. 1, 1999, "SU5416 is a Potent and Selective Inhibitor of the Vascular Endothelial Growth Factor Receptor (Flk-1/KDR) That inhibits Tyrosine Kinase Catalysis, Tumor Vascularization, and Growth of Multiple Tumor Types".

Ferrara, N. et al., Nature Medicine, vol. 5, No. 12, pp. 1359-1364, Dec. 1999, "Clinial applications of angiogenic growth factors and their inhibitors".

Presta, L. G. et al., Cancer Research, vol. 57, pp. 4593-4599, Oct. 5, 1997, "Humanization of an Anti-Vascular Endothelial Growth Factor Monoclonal Antibody for the Therapy of Solid Tumors and Other Disorders".

Browder, T. et al., Cancer Research, vol. 60, No. 7, pp. 1777-2065, Apr. 2000, "Antiangiogenic Scheduling or Chemotherapy Improves Efficacy Against Experimental Drug-resistant Cancer".

Witte, L. et al., Cancer Metastasis Rev., vol. 17, pp. 155-161, (1998), "Monoclonal antibodies targeting the VEGF receptor-2 (Flk1/KDR) as an anti-angiogenic therapeutic strategy".

Kohler, G. and Milstein, C., Nature, vol. 256, No. 5516, pp. 495-497. Jul. 1975, "Continuous cultures of fused cells secreting antibody of predefined specificity".

Cole, S.P.C. et al., Monoclonal Antibodies and Cancer Therapy, pp. 77-96 , Feb. 1985, "The EBV-Hybridoma Technique and its Application to Human Lung Cancer".

Berman, J. E. et al., EMBO J. vol. 7, No. 3, pp. 727-738, Mar. 1988, "Content and organization of the human Ig $V_H$ locus: definition of three new $V_H$ Families and linkage to the Ig $C_H$ locus".

Gillam, S. and Smith, M. Gene, vol. 8, No. 1, pp. 81-97, Dec. 1979, "Site-Specific Mutagenesis Using Synthetic Oligodeoxyribonucleotide Primers: I. Optimum Conditions and Minimum Oligodeoxyribonucleotide Length".

Roberts, J. et al., Nature, vol. 328, No. 6132, pp. 73 1-734, Aug. 1987, "Generation of an antibody with enhanced affinity and specificity for its antigen by protein engineering".

Sung Co, M. and Queen C., Nature, vol. 351, No. 6326, pp. 501-502, Jun. 1991, "Humanized antibodies for therapy".

Gerber, H. P. et al., The Journal of Biological Chemistry, vol. 273, No. 46, Nov. 13, pp. 30336-30343, 1998, "Vascular Endothelial Growth Factor Regulates Endothelial Cell Survival through the Phosphatidylinositol 3'-Kinase/Akt Signal Transduction Pathway".

Hata, Y. et al., Diabetes. vol. 18, pp. 1145-1155, May 1999, "Basic Fibroblast Growth Factor Induces Expression of VEGF Receptor KDR Through a Protein Kinase C and p44/p42 Mitogen-Activated Protein Kinase-Dependent Pathway".

Inaba, M. et al, Cancer vol. 64, pp. 1577-1582, 1989, "Evaluation of Antitumor Activity in a Human Breast Tumor / Nude Mouse Model With a Special Emphasis on Treatment Dose".

Teicher, B. A. et al., Int. Journal of Cancer, vol. 57, No. 6, Jun. 15, 1994, "Potentiation of Cytotoxic Cancer Therapies by TNP-470 Alone And With Other Anti-Angiogenic Agents".

Kakeji, Y. et al., Investigational New Drugs, vol. 15, pp. 39-48, 1997, "Preclinical studies of the combination of angiogenic inhibitors with cytotoxic agents".

Teicher, B. A. et al., Cancer Research, vol. 52, No. 23, pp. 6702-6704. Dec. 1, 1992, "Antiangiogenic Agents Potentiate Cytotoxic Cancer Therapies against Primary and Metastatic Disease".

Tamm, I. et al., Cancer Research, vol. 58, pp. 5315-5320, Dec. 1, 1998, "IAP-Family Protein Survivin Inhibits Caspase Activity and Apoptosis Induced by Fas (CD95), Bax, Caspases, and Anticancer Drugs".

Yuan, F. et al., Medical Sciences, vol. 93, pp. 14765-14770, Dec. 1996, "Time-dependent vascular regression and permeability changes in established human tumor xenografts induced by an anti-vascular endothelial growth factor/vascular permeability factor antibody".

Baguley, B. C. et al., Eur. J. Cancer, vol. 27, No. 4, pp. 482-487, 1991, "Inhibition of growth of Colon 38 Adenocarcinoma by Vinblastine and Colchicine: Evidence for a Vascular Mechanism".

O'Leary, J. J. et al., Clinical Cancer Research, vol. 5, pp. 181-187, Jan. 1999, Antiangiogenic Effects of Camptothecin Analogues 9-Amino-20(S)-camptothecin, Topotecan, and CPT-11 Studied in the Mouse Cornea Model.

Asahara, T. et al., The EMBO Journal, vol. 18, No. 14, pp. 3964-3972, 1999, "VEGF contributes to postnatal neovascularization by mobilizing bone marrow-derived endothelial progenitor cells".

Tran, T. et al., Biochemical and Biophysical Research Communications, vol. 264, pp. 781-788, 1999, "Marked Induction of the IAP Family Antiapoptotic Proteins Survivin and XIAP by VEGF in Vascular Endothelial Cells".

Nor, J. E. et al, American Journal of Pathology, vol. 154, No. 2 Feb. 1999, "Vascular Endothelial Growth Factor (VEGF)-Mediated Angiogenesis Is Associated with Enhanced Endothelial Cell Survival and Induction of Bcl-2 Expression".

Belotti, D. et al., Clinical Cancer Research, vol. 2, pp. 1843-1849, Nov. 1996; "The Microtubule-affecting Drug Paclitaxel Has Antiangiogenic Activity".

Kaban. L. B. et al., Pediatrics, vol. 103, No. 6, Jun. 1999, "Antiangiogenic Therapy of a Recurrent Giant Cell Tumor of the Mandible With Interferon Alfa-2a".

Slaton, J. W. et al., Clinical Cancer Research, vol. 5, pp. 2726-2734, Oct. 1999, "Interferon-α-mediated Down-Regulation of Angiogenesis-related Genes and Therapy of Baldder Cancer Are Dependent on Optimization of Biological Dose and Schedule".

Gorski, D. H. et al., Cancer Research, vol. 59, pp. 3374-3378, Jul. 15, 1999, "Blockade of the Vascular Endothelial Growth Factor Stress Response Increases the Antitumor Effects of Ionizing Radiation".

Boehm. T. et al., Nature, vol. 390, Nov. 27, 1997, pp. 237-239, "Antiangiogenic therapy of experimental cancer does not induce acquired drug resistance".

Mauceri, H. J. et al., Nature, vol. 394, Jul. 16, 1998, Combined effects of angiostatin and ionizing radiation antitumor therapy.

Database PROMT, Accession No. 1999:838616, ImClone Systems, Inc. Imclone Files Investigational New Drug Application for Anti-Angiogenesis. Business Wire, Dec. 15, 1999.

DeVita et al., Cancer: Principles & Practice of Oncology, $5^{th}$ edition, 1997, pp. 333, 405, 418, 432.

* cited by examiner

FIGURE 1

HindIII
_GAACTT_ATGGGATGGTCATGTATCATCCTTTTTCTAGTAGCAACTGCAACTGGAGTACAT
      M  G  W  S  C  I  I  L  F  L  V  A  T  A  T  G  V  H
               leader TCACAGGTCAAGCTGCAGCAGTCTGGGGCAGAGCTTGTGGGGTCAGGGGCCTCAGTCAAA
 S  Q  V  K  L  Q  Q  S  G  A  E  L  V  G  S  G  A  S  V  K
    VH TTGTCCTGCACAACTTCTGGCTTCAACATTAAAGACTTCTATATGCACTGGGTGAAGCAG
 L  S  C  T  T  S  <u>G  F  N  I  K  D  F  Y  M  H</u>  W  V  K  Q
                        CDR-H1

AGGCCTGAACAGGGCCTGGAGTGGATTGGATGGATTGATCCTGAGAATGGTGATTCTGAT
 R  P  E  Q  G  L  E  W  I  G  <u>W  I  D  P  E  N  G  D  S  D</u>
                                 CDR-H2

TATGCCCCGAAGTTCCAGGGCAAGGCCACCATGACTGCAGACTCATCCTCCAACACAGCC
 <u>Y  A  P  K  F  Q  G</u>  K  A  T  M  T  A  D  S  S  S  N  T  A

TACCTGCAGCTCAGCAGCCTGACATCTGAGGACACTGCCGTCTATTACTGTAATGCATAC
 Y  L  Q  L  S  S  L  T  S  E  D  T  A  V  Y  Y  C  N  A  <u>Y</u>

TATGGTGACTACGAAGGCTACTGGGGCCAAGGGACCACGGTCACCGTCTCCTCAGGTGAG
 <u>Y  G  D  Y  E  G  Y</u>  W  G  Q  G  T  T  V  T  V  S  S
     CDR-H3

BamHI
_TGGATCC_

HindIII
_AAGCTT_ATGGGATGGTCATGTATCATCCTTTTTCTAGTAGCAACTGCAACTGGAGTACAT
      M  G  W  S  C  I  I  L  F  L  V  A  T  A  T  G  V  H
               leader TCAGACATCGAGCTCACTCAGTCTCCAGCAATCATGTCTGCATCTCCAGGGGAGAAGGTC
 S  D  I  E  L  T  Q  S  P  A  I  M  S  A  S  P  G  E  K  V
    VL ACCATAACCTGCAGTGCCAGCTCAAGTGTAAGTTACATGCACTGGTTCCAGCAGAAGCCA
 T  I  T  C  <u>S  A  S  S  S  V  S  Y  M  H</u>  W  F  Q  Q  K  P
             CDR-L1

GGCACTTCTCCCAAACTCTGGATTTATAGCACATCCAACCTGGCTTCTGGAGTCCCTGCT
 G  T  S  P  K  L  W  I  Y  <u>S  T  S  N  L  A  S</u>  G  V  P  A
                           CDR-L2

CGCTTCAGTGGCAGTGGATCTGGGACCTCTTACTCTCTCACAATCAGCCGAATGGAGGCT
 R  F  S  G  S  G  S  G  T  S  Y  S  L  T  I  S  R  M  E  A
GAAGATGCTGCCACTTATTACTGCCAGCAAAGGAGTAGTTACCCATTCACGTTCGGCTCG
 E  D  A  A  T  Y  Y  C  <u>Q  Q  R  S  S  Y  P  F  T</u>  F  G  S
                              CDR-L3

FIGURE 1 CONTINUED

```
                                          BamHI
GGGACCAAGCTGGAAATAAAACGTGAGTGGATCC
  G   T   K   L   E   I   K
```

THERAPEUTIC METHOD FOR REDUCING ANGIOGENESIS

The present application claims the benefit of priority from U.S. Provisional Application No. 60/178,791, filed on Jan. 28, 2000, which is hereby incorporated in its entirety by reference.

FIELD OF THE INVENTION

The present invention relates to the inhibition or prevention of angiogenesis as a means to control or treat an angiogenic dependent condition, a condition characterized by, or dependent upon, blood vessel proliferation. The invention further relates to the use of an anti-angiogenic molecule in combination with a chemotherapeutic agent.

BACKGROUND OF THE INVENTION

Angiogenesis is a highly complex process of developing new blood vessels that involves the proliferation and migration of, and tissue infiltration by capillary endothelial cells from pre-existing blood vessels, cell assembly into tubular structures, joining of newly forming tubular assemblies to closed-circuit vascular systems, and maturation of newly formed capillary vessels. The molecular bases of many of these aspects are still not understood.

Angiogenesis is important in normal physiological processes including embryonic development, follicular growth, and wound healing, as well as in pathological conditions such as tumor growth and in non-neoplastic diseases involving abnormal neovascularization, including neovascular glaucoma (Folkman, J. and Klagsbrun, M. Science 235:442-447 (1987). Other disease states include but are not limited to, neoplastic diseases, including but not limited to solid tumors, autoimmune diseases and collagen vascular diseases such as, for example, rheumatoid arthritis, and ophthalmalogical conditions such as diabetic retinopathy, retrolental fibroplasia and neovascular glaucoma. Conditions or diseases to which persistent or uncontrolled angiogenesis contribute have been termed angiogenic dependent or angiogenic associated diseases.

One means of controlling such diseases and pathological conditions comprises restricting the blood supply to those cells involved in mediating or causing the disease or condition. For example, in the case of neoplastic disease, solid tumors develop to a size of about a few millimeters, and further growth is not possible, absent angiogenesis within the tumor. In the past, strategies to limit the blood supply to tumors have included occluding blood vessels supplying portions of organs in which tumors are present. Such approaches require the site of the tumor to be identified and are generally limited to treatment to a single site, or small number of sites. An additional disadvantage of direct mechanical restriction of a blood supply is that collateral blood vessels develop, often quite rapidly, restoring the blood supply to the tumor.

Other approaches have focused on the modulation of factors that are involved in the regulation of angiogenesis. While usually quiescent, vascular endothelial proliferation is highly regulated, even during angiogenesis. Examples of factors that have been implicated as possible regulators of angiogenesis in vivo include, but are not limited to, transforming growth factor beta (TGFβ), acidic and basic fibroblast growth factor (aFGF and bFGF), platelet derived growth factor (PDGF), and vascular endothelial growth factor (VEGF) (Klagsbrun, M. and D'Amore, P. (1991) Annual Rev. Physiol. 53: 217-239).

One growth factor of particular interest is VEGF. An endothelial-cell specific mitogen, VEGF acts as an angiogenesis inducer by specifically promoting the proliferation of endothelial cells. It is a homodimeric glycoprotein consisting of two 23 kD subunits with structural similarity to PDGF. Four different monomeric isoforms of VEGF resulting from alternative splicing of mRNA have been identified. These include two membrane bound forms ($VEGF_{206}$ and $VEGF_{189}$) and two soluble forms ($VEGF_{165}$, and $VEGF_{121}$). $VEGF_{165}$ is the most abundant isoform in all human tissues except placenta.

VEGF is expressed in embryonic tissues (Breier et al., Development (Camb.) 114:521 (1992)), macrophages, and proliferating epidermal keratinocytes during wound healing (Brown et al., J. Exp. Med., 176:1375 (1992)), and may be responsible for tissue edema associated with inflammation (Ferrara et al., Endocr. Rev. 13:18 (1992)). In situ hybridization studies have demonstrated high levels of VEGF expression in a number of human tumor lines including glioblastoma multiforme, hemangioblastoma, other central nervous system neoplasms and AIDS-associated Kaposi's sarcoma (Plate, K. et al. (1992) Nature 359: 845-848; Plate, K. et al. (1993) Cancer Res. 53: 5822-5827; Berkman, R. et al. (1993) J. Clin. Invest. 91: 153-159; Nakamura, S. et al. (1992) AIDS Weekly, 13 (1)). High levels of VEGF also have been reported in hypoxia induced angiogenesis (Shweiki, D. et al. (1992) Nature 359: 843-845).

VEGF mediates its biological effect through high affinity VEGF receptors which are selectively expressed on endothelial cells during, for example, embryogenesis (Millauer, B., et al. (1993) Cell 72: 835-846) and tumor formation. VEGF receptors typically are class III receptor-type tyrosine kinases characterized by having several, typically 5 or 7, immunoglobulin-like loops in their amino-terminal extracellular receptor ligand-binding domains (Kaipainen et al., J. Exp. Med. 178: 2077-2088 (1993)). The other two regions include a transmembrane region and a carboxy-terminal intracellular catalytic domain interrupted by an insertion of hydrophilic interkinase sequences of variable lengths, called the kinase insert domain (Terman et al., Oncogene 6:1677-1683 (1991)). VEGF receptors include flt-1, sequenced by Shibuya M. et al., Oncogene 5, 519-524 (1990); flk-1, sequenced by Matthews W. et al. Proc. Natl. Acad. Sci. USA, 88:9026-9030 (1991) and KDR, the human homologue of flk-1, described in PCT/US92/01300, filed Feb. 20, 1992, and in Terman et al., Oncogene 6:1677-1683 (1991).

High levels of flk-1 are expressed by endothelial cells that infiltrate gliomas (Plate, K. et al., (1992) Nature 359: 845-848), and are specifically upregulated by VEGF produced by human glioblastomas (Plate, K. et al. (1993) Cancer Res. 53: 5822-5827). The finding of high levels of flk-1 expression in glioblastoma associated endothelial cells (GAEC) suggests that receptor activity is induced during tumor formation, since flk-1 transcripts are barely detectable in normal brain endothelial cells. This upregulation is confined to the vascular endothelial cells in close proximity to the tumor. Blocking VEGF activity with neutralizing anti-VEGF monoclonal antibodies (mAbs) results in inhibition of the growth of human tumor xenografts in nude mice (Kim, K. et al. (1993) Nature 362: 841-844), suggesting a direct role for VEGF in tumor-related angiogenesis.

Various chemotherapeutic drugs also have been shown to block functions of activated, dividing endothelial cells critical to angiogenesis, or to kill such cells. Such collateral damaging effects on a genetically stable normal host cell, in addition to the chemotherapeutic agent's effect upon the tumor cells, contribute significantly to the in vivo anti-tumor efficacy of chemotherapy. However, the standard use of chemotherapeutic agents has obvious undesirable side-effects upon the normal cells of patients, limiting its use. Administration of chemotherapeutic agents in their usual doses and at usual dosage frequencies are commonly associated with side-effects, including, but not limited to, myelosuppression, neurotoxicity, cardiotoxicity, alopecia, nausea and vomiting, nephrotoxicity, and gastrointestinal toxicity. Further, patients' tumors often also develop resistance to the chemotherapeutic agents after initial exposure to the drugs.

A desirable method and composition for controlling angiogenesis should be well tolerated, have few or no side-effects, and prevent new vessel formation at sites of disease without interfering with required physiologic angiogenesis in normal sites. It should be effective and, in the case of neoplastic disease, overcome the problem of the development of drug resistance by tumor cells. In so doing, it should permit targeted therapy without the accurate identification of all disease sites. The present invention addresses many of the problems with existing materials and methods.

SUMMARY OF THE INVENTION

The present invention provides a method of treating an angiogenic dependent condition in a mammal comprising administering an anti-angiogenic molecule and a chemotherapeutic agent to the mammal, in an amount and frequency effective, in combination, to produce a regression or arrest of the condition without significant toxicity from the chemotherapeutic agent. The angiogenic dependent condition may be selected from the group consisting of neoplasm, collagen-vascular disease or auto-immune disease, including a solid tumor neoplasm, including breast carcinoma, lung carcinoma, prostate carcinoma, colon carcinoma, prostate carcinoma, ovarian carcinoma, neuroblastoma, central nervous system tumor, neuroblastoma, glioblastoma multiforme or melanoma. The mammal receiving the treatment is preferably a human.

The anti-angiogenic molecules inhibit the action of a vascular endothelium survival factor, which include receptors and their ligands. Vascular endothelium survival factors include receptors, including angiogenic growth factors such as VEGF receptor, including flk-1/KDR receptor, or flt-4 receptor and VEGF. Examples of other vascular endothelial survival factors are integrin $\alpha_v\beta_3$, $\alpha_v\beta_3$ ligand, Tie2/tek ligand, Tie2/tek, endoglin ligand, endoglin, neuropilin ligand, neuropilin, thrombospondin ligand, thrombospondin, PDGF$\alpha$, PDGF$\alpha$ receptor, PDGF$\beta$, PDGF$\beta$ receptor, aFGF, aFGF receptor, bFGF, bFGF receptor, TGF$\beta$, TGF$\beta$ receptor, EGF, EGF receptor, angiostatin, angiostatin receptor, angiopoetin, angiopoeitin receptor, PLGF, PLGF receptor, VPF, or VPF receptor. Optionally, the ligand is selected from the group consisting of VEGF (VEGF-A), VEGF-B, VEGF-C, or VEGF-D. The anti-angiogenic molecule may be selected from the group consisting of antibody, antibody fragment, small molecule or peptide.

Preferred embodiments of the present invention include antibodies selected from the group consisting of mouse antibody, rat antibody, chimeric antibody, humanized antibody or human antibody. A preferred antibody is IMC-1C11.

Preferably, IMC-1C11 is administered in a dose of from about 5 mg/m$^2$ to about 700 mg/m$^2$ about daily to about every 7 days, more preferably a dose of from about 7.5 mg/m$^2$ to about 225 mg/m$^2$, about twice per week. Optionally, the IMC-1C11 is administered at a dose and frequency sufficient to substantially saturate the VEGF receptor. Optionally, the anti-angiogenic molecule is administered in a dose and frequency sufficient to substantially saturate the target of the anti-angiogenic molecule. In another embodiment, the anti-angiogenic molecule is administered in a dose equivalent to that of IMC-1C11, administered in a dose of from about 5 mg/m$^2$ to about 700 mg/m$^2$ about daily to about every 7 days, more preferably a dose of from about 7.5 mg/m$^2$ to about 225 mg/m$^2$, about twice per week.

The chemotherapeutic agent may be selected from the group consisting of vinca alkaloid, camptothecan, taxane, or platinum analogue, including vincristine, vinblastine, vinorelbine, vindesine, paclitaxel, docetaxel, 5 FU, cisplatin, carboplatin, irinotecan, topotecan or cyclophosphamide. The chemotherapeutic agent is administered in a low-dose regimen. Preferably the chemotherapeutic agent is administered at less than about 20% of the maximum tolerated dose, more preferably at less than about 15% of the maximum tolerated dose, more preferably at less than about 10% of the maximum tolerated dose, more preferably at less than about 5% of the maximum tolerated dose, and most preferably at less than about 2% of the maximum tolerated dose. In one embodiment of the invention the chemotherapeutic agent is administered at a dose intensity less than about 20% of the dose intensity of the chemotherapeutic agent when used in a conventional chemotherapeutic regimen, preferably at a dose intensity less than about 10% of the dose intensity of the chemotherapeutic agent when used in a conventional chemotherapeutic regimen, and more preferably at a dose intensity less than about 5% of the dose intensity of the chemotherapeutic agent when used in a conventional chemotherapeutic regimen.

In one preferred embodiment the vinblastine is administered in a dose from about 0.5 mg/m$^2$ to about 3 mg/m$^2$ from about once every 3 days to about once every 7 days. In another embodiment, the chemotherapeutic agent is administered in a dosage and frequency that is of substantially equivalent efficacy to vinblastine in a dose from about 0.5 mg/m$^2$ to about 3 mg/m$^2$ from about once every 3 days to about once every 7 days. Optionally the chemotherapeutic agent is administered more frequently than about every three weeks, or more frequently than about every seven days.

The present invention also includes a kit for treating an angiogenic dependent condition in a mammal comprising the anti-angiogenic molecule and the chemotherapeutic agent, which are provided to be administered in an amount and frequency effective, in combination, to produce a regression or arrest of the condition while minimizing or preventing significant toxicity of the chemotherapeutic agent.

BRIEF DESCRIPTION OF FIGURES

FIG. 1 is the encoding nucleotide sequence and deduced amino acid sequence of $V_H$ and $V_L$ domains of IMC-1C11 (c-p1C11).

DETAILED DESCRIPTION OF THE INVENTION

Throughout this application, various articles and patents, and patent application are referenced. Disclosures of all of these publications in their entireties are hereby incorporated by reference into this application.

The present invention comprises a method of treating or controlling an angiogenic dependent condition in a mammal, comprising administering an anti-angiogenic molecule and a chemotherapeutic agent in amounts and frequencies effective to produce, in combination, a regression or arrest of the angiogenic dependent condition, while minimizing or preventing significant toxicity.

The benefits of the combination of an anti-angiogenic molecule and a chemotherapeutic agent of the present invention include an improvement in the treatment and control of an angiogenic dependant condition with reduced doses of a chemotherapeutic agent administered at increased frequency, without significant toxicity. The combination can be administered for a prolonged period of time, or optionally a shorter duration of treatment may be administered due to the increased effectiveness of the combination. Toxicity is reduced or eliminated without a loss of effectiveness. The administration of the treatment of the invention can overcome the problems of drug resistance that develops with standard chemotherapeutic regimens.

The anti-angiogenic molecule functions to inhibit or prevent angiogenesis, thereby treating or controlling the angiogenic dependent condition by inhibiting or blocking (antagonizing) the effect of vascular endothelial survival factors. These survival factors are receptors or their ligands, upon which vascular endothelium depends, either directly or indirectly, for growth and/or survival. They play a role in allowing vascular endothelial cells to recovery from injury or insult, which, absent the effect of the survival factor would result in cell death or apoptosis. Survival factors include vascular endothelial cell growth factors or mitogens, as well as those factors which do not appear to have a direct growth-stimulatory effect but allow the cells to recover from injury.

The survival factors that are receptors are located on vascular endothelial cells or optionally, may be located on other cell types including, but not limited to tumor cells. The anti-angiogenic molecule inhibit binding to, and/or activation of, receptors, inhibit their expression, or inhibit the binding or expression of ligands.

Examples of survival factors include VEGF receptors, including but not limited to flt-1 (VEGFR1), flk-1/KDR (VEGFR2), flt-4 (VEGFR3), their ligands VEGF, VEGF-B, VEGF-C, and VEGF-D, integrin $\alpha_v\beta_3$, Tie2/tek, endoglin (CD105), neuropilin, thrombospondin and their ligands, and PDGF$\alpha$, PDGF$\beta$, aFGF, bFGF, and TGF$\beta$, as well as EGF, angiostatin, and angiopoeitin, vascular permeability factor (VPF), and placenta-like growth factor (PLGF) and their receptors.

Suitable types of anti-angiogenic molecules include, but are not limited to antibody, antibody fragment, small molecule or peptide. An antibody can be derived from any mammalian species. Optionally, the antibody is of mouse, rat, rabbit, or human origin. Preferably the antibody is chimeric, more preferably the antibody is humanized, and even more preferably the antibody is human. Suitable antibody fragments include, for example, Fab fragment, Fab' fragment, F(ab')$_2$ fragment, monovalent single chain antibody (scFv), and diabodies (DAB).

Examples of suitable anti-angiogenic molecules that are antagonists to vascular endothelium survival factors include, but are not limited to, VEGF receptor antagonist or VEGF antagonist, as disclosed in U.S. Pat. Nos. 5,840,301, 5,861,499, 5,874,542, 5,955,311, and 5,730,977, which are incorporated in their entirety by reference, aFGF receptor antagonist, aFGF antagonist, bFGF receptor antagonist, bFGF antagonist, PDGF receptor antagonist, PDGF antagonist, TGF$\beta$ antagonist, Tie2/tek antagonist (P. Lin et al., Inhibition of Tumor Angiogenesis Using a Soluble Receptor Establishes a Role for Tie2 in Pathologic Vascular Growth. *J. Clin. Invest.* 100(8) 2072 (1997)), endoglin (CD105) antagonist, as disclosed in U.S. Pat. Nos. 5,855,866, and 5,660,827, neuropilin antagonist, thrombospondin antagonist, and antagonists to the receptors for PDGF$\alpha$, PDGF$\beta$, aFGF, bFGF, or TGF$\beta$, as well as antagonists to the receptors for EGF, angiostatin, angiopoeitin, or VPF (Vascular Permeability Factor) as disclosed in U.S. Pat. Nos. 5,036,003 and 5,659,013. Also encompassed within the scope of the present invention are integrin receptor antagonists as disclosed in U.S. Pat. Nos. 6,017,926, 6,017,925, 5,981,546, 5,952,341, and 5,919,792, integrin $\alpha_v\beta_3$ antagonists, as disclosed in U.S. Pat. Nos. 5,780,426, 5,773,412, 5,767,071, 5,759,996, 5,753,230, 5,652,110, and 5,652,109, antagonists to placenta-like growth factor (PLGF) as disclosed in European Patent Application EP506477A1, thrombospondin antagonists as disclosed in U.S. Pat. Nos. 5,840,692, 5,770,563, 5,654,277, 5,648,461, 5,506,208, 5,399,667, 5,200,397, 5,192,744, and 5,190,918, as well as those disclosed in U.S. Pat. Nos. 5,965,132, 6,004,555 and 5,877,289, and PCT Applications Nos. WO 99/16465, WO 97/05250, WO 98/33917. Also included are molecules such as thalidomide, TNP-470, interferon-$\alpha$ (INF-$\alpha$), and interleukin-12 (IL-12).

In many cases, the expression of a receptor and/or ligand is upregulated in an region of angiogenesis. However, although located in an area of abnormal cells responsible for the specific disease, exposed to high levels of ligand, and having upregulated receptors, the cells of the vascular endothelium are largely normal and responsive to normal regulatory mechanisms. Because the receptors exist on essentially normal endothelial cells, their behavior is less likely to escape normal regulatory control. An advantage to blocking a receptor, rather than its ligand, is that fewer anti-angiogenic molecules may be needed to achieve such inhibition, as levels of receptor expression may be more constant than those of the environmentally induced ligand. Although there are advantages to targeting receptors, it is also possible, and within the scope of the present invention, to inhibit angiogenesis by targeting the ligand for the receptor, either alone or in combination with blockade of the receptor. Optionally, antagonism of the receptor is combined with antagonism of the ligand in order to achieve even more efficient inhibition of angiogenesis.

A preferred embodiment of the invention is the combination of a chemotherapeutic agent and a VEGF receptor antagonist. It has been shown that a major function of VEGF is to promote the survival of endothelial cells comprising newly formed vessels (L. E. Benjamin, et Al., Selective Ablation of Immature Blood Vessels in Established Human Tumors Follows Vascular Endothelial Growth Factor Withdrawal. *J. Clin. Invest.* 103:159-165 (1999), T. Alon, et al., Vascular Endothelial Growth Factor Acts as a Survival Factor for Newly Formed Retinal Vessels and Has Implications for Retinopathy of Prematurity. *Nature Med.* 1:1024-1028 (1995), R. K. Jain, et al., Endothelial Cell Death, Angiogenesis, and Microvascular Function after Castration in an Androgen-Dependent Tumor: Role of Vascular Endothelial Growth Factor. *Proc. Natl. Acad. Sci. U.S.A.* 95:10820-10825 (1998)) Hence, the ability of such cells to cope with the damage inflicted by continuous or frequent exposure to a chemotherapeutic drug is selectively and significantly impaired when they are exposed to a VEGF receptor antagonist, (M. J. Prewett, et al., Antivascular Endothelial Growth Factor Receptor (Fetal Liver Kinase 1) Monoclonal Antibody Inhibits Tumor Angiogenesis and Growth of Several Mouse and Human Tumors. *Cancer Res* 59:5209-5218. (1999); T. A. Fong, et al., SU5416 Is a Potent and Selective Inhibitor of the Vascular Endothelial Growth Factor Receptor (Flk-1/kdr) That Inhibits Tyrosine Kinase Catalysis, Tumor Vascularization, and Growth of Multiple Tumor Types. *Cancer Res* 59:99-106 (1999); N. Ferrara, et al., Clinical Applications of Angiogenic Growth Factors and Their Inhibitors. Nat. Med. 5:1359-1364. (1999)). It is believed that the combination of continuous or frequent chemotherapy with, for example, interruption of the cell rescue mechanisms provided by activation of the VEGF receptor plays a role in inducing vascular endothelial cell apoptosis.

In a preferred embodiment of the invention, the anti-angiogenic molecule is an antagonist to VEGF or the VEGF receptor. While the expression of the VEGF receptor and ligand is low in normal endothelial cells that are not in or near a region of angiogenesis, VEGF receptors present on tumor infiltrating vascular endothelial cells are upregulated, as is the expression of the VEGF ligand by tumor cells. Blocking the interaction between VEGF and its receptors can inhibit angiogenesis, and thereby tumor growth, while not significantly effecting normal endothelial cells at other sites, where vascular endothelial cell receptors have not been upregulated. In one embodiment of the present invention, antagonism of the VEGF receptor is combined with antagonism of the VEGF ligand in order to achieve even more efficient inhibition of angiogenesis. In other embodiments of the invention antagonists to one or more than one of the VEGF receptors or ligands are administered. VEGF (or VEGF-A) is the ligand for VEGFR1 and VEGFR2, VEGF-B is the ligand for VEGFR2, VEGF-C is the ligand for VEGFR3, VEGFR4, and possibly VEGFR2, and VEGF-D is the ligand for VEGFR2 and VEGFR3. Optionally, the effect of more than one form of VEGF is inhibited.

An example of an antagonist to a VEGF receptor (flk-1) is the antibodies DC101, described in the Examples. Another is A.4.6.1 and its chimeric and humanized form as disclosed in L. G. Presta, Humanization of an Anti-vascular Endothelial Growth Factor Monoclonal Antibody for the Therapy of Solid Tumors and Other Disorders. *Cancer Research,* 57, 4593-4599 (1997), which is hereby incorporated by reference. A preferred VEGF antagonist is the mouse-human chimeric antibody IMC-1C11 which is a KDR antagonist, and is disclosed in U.S. application Ser. No. 09/240,736, which is hereby incorporated by reference. The encoding nucleotide sequences and deduced amino acid sequences of the $V_H$ and $V_L$ domains are shown in FIG. 1.

The chemotherapeutic agent of the present invention functions, in combination with the anti-angiogenic molecule, to cause a cytotoxic effect on the vascular endothelial cells involved in angiogenesis. A number of chemotherapeutic agents have been identified as having anti-angiogenic activity and are suitable for use in the practice of the present invention. Examples include, but are not limited to, taxanes, including but not limited to paclitaxel and docetaxel, camptothecin analogues, including but not limited to irinotecan and topotecan, platinum analogues including but not limited to cisplatin and carboplatin, 5FU, and vinca alkaloids, including but not limited to vinblastine, vincristine, vindesine and vinorelbine.

The present invention provides a low dose application of a chemotherapeutic agent administered in combination with an anti-angiogenic molecule in an amount and frequency that, in combination, provides effective therapy without significant side-effects. Effective therapy is therapy that provides regression or arrest of the angiogenic dependant condition. An effective amount of anti-angiogenic molecule and chemotherapeutic agent is an amount of each, that in combination controls (causes regression or arrest) the condition being treated without producing significant chemotherapy induced toxicity. The meaning of significant toxicity is well known to one of ordinary skill in the art, and includes toxicities that cumulatively or acutely effect a patient's quality of life and/or limit the amount of chemotherapeutic agent than can be administered.

Examples of chemotherapy induced toxicity that can be minimized or prevented by the present invention include, but are not limited to, myelosuppression, neurotoxicity, cardiotoxicity, alopecia, nausea and vomiting, nephrotoxicity, and gastrointestinal toxicity. The low dose administration of a chemotherapeutic agent without significant toxicity permits prolonged treatment if desired. Additionally, the low dose manner of chemotherapy administration in the present invention can overcome the problem of the development of chemotherapeutic drug resistance by the patient's tumor cells that occurs with current chemotherapeutic regimens which consist of higher doses of drug administered intermittently with longer time intervals between treatment. The present invention delays, reduces, or even circumvents the problem of acquired drug resistance by targeting the genetically stable endothelial cells of newly formed tumor blood vessels, rather than genetically unstable tumor cells which are prone to mutate and develop resistance. Encompassed within the scope of the present invention is the administration of amounts of chemotherapy that are insufficient to have a cytotoxic effect on tumor cells yet have anti-angiogenic properties as a result of the drug's effect on vascular endothelial cells.

The low-dose administration of chemotherapeutic agents, to achieve therapeutic effects without significant toxicity (side effects) is readily possible by the practice of the present invention. Applying standard methods of defining optimal dosage levels and schedules to the teachings of the present invention, one of ordinary skill in the art readily can determine a more or most desirable low-dose regimen for a selected chemotherapeutic agent when used in combination with an anti-angiogenic molecule, as detailed in the present application. A low-dose regimen will administer the chemotherapy at frequent intervals or continually, at less than about 50% of the maximum tolerated dose (MTD), more preferably less than about 45% of the MTD, more preferably less than about 40% of the MTD, more preferably less than about 35% of the MTD, more preferably less than about 30% of the MTD, more preferably at less than about 25% of the MTD, more preferably at less than about 20% of the MTD, more preferably at less than about 10% of the MTD more preferably less than about 5% of the MTD, and most preferably at less than about 2% of the MTD, although the preferred dose depends on the particular chemotherapy. In any event, the preferred dose will be a dose effective to inhibit or prevent progression of the angiogenic dependent condition, when administered in combination with the anti-angiogenic molecule of the present invention, while minimizing or preventing the development of significant chemotherapy related toxicity. Optionally the dose of chemotherapy will be effective to inhibit or prevent progression of the angiogenic dependent condition even when administered alone, although it is not intended that it be administered in this manner. Optionally the dose of chemotherapy will be one which is sufficiently low that it does not exert a direct cytotoxic effect on tumor cells, yet has an antitumor effect mediated by its anti-angiogenic properties.

Optionally, the low-dose regimen of the present invention will administer the chemotherapeutic agent at a dose intensity of less than about 20% of the dose intensity used when the chemotherapeutic agent is administered as part of a conventional chemotherapeutic regimen (i.e. administered at conventional dosages and frequencies without an anti-angiogenic molecule or other treatment modality) used to treat a particular neoplasm. The dose intensity of the chemotherapeutic agent used in a conventional regimen can be readily determined by one of ordinary skill in the art. By way of example, various regimens are disclosed in V. T. Devita et al.,

*Cancer: Principles & Practice of Oncology*, 5th edition, Lippencott Williams and Wilkins. (1997) More preferably the present invention will administer the chemotherapeutic agent at a dose intensity of less than about 10% of that used when the chemotherapeutic agent is administered as part of a conventional chemotherapeutic regimen used to treat a particular neoplasm, and most preferably at a dose intensity of less than about 5% of that used when the chemotherapeutic agent is administered as part of a conventional chemotherapeutic regimen used to treat a particular neoplasm.

In the prior art, chemotherapy is usually given intermittently, commonly in the form of a bolus infusion or an infusion lasting from about 20 minutes to about three hours, at about the maximum tolerated dose (MTD) with long rest periods (e.g., 3 weeks) between successive drug exposures. It has been suggested that these rest periods provide the endothelial cell compartment of a tumor an opportunity to repair some of the damage inflicted by the chemotherapy (T. Browder, et al., Antiangiogenic Scheduling of Chemotherapy Improves Efficacy Against Experimental Drug-Resistant Cancer. Cancer Res 60: 1878-1886, Apr. 1, 2000. Administering lower doses of a chemotherapeutic drug more frequently such as weekly, more preferably several times a week or continuously, enables circumvention of many problems associated with standard chemotherapeutic doses. This anti-angiogenic scheduling of chemotherapy optimizes anti-vascular effects. An added benefit is that administration of chemotherapy in this manner can result in the increased sensitivity of the tumor cells to chemotherapy. For example, a sub-line of the Lewis Lung Carcinoma, previously selected in vivo for acquired resistance to the MTD of cyclophosphamide, is rendered sensitive again to the drug in vivo by employing continuous low dose therapy of the same drug. The inclusion of the anti-angiogenic molecule of the present invention provides substantial and unexpectedly better results.

The invention provides low-dose administration of chemotherapy administered at short intervals, preferably more frequently than every three weeks, more preferably more frequently than weekly. Most preferably it is administered from about every 4 to about every 6 hours, to about daily to weekly. Optionally it is administered continuously. The preferred time interval between administration of successive doses of chemotherapeutic agent is that amount of time that is of sufficiently short duration that the blood levels of the chemotherapeutic agent (or its active metabolite) will remain at about a concentration sufficient to exert an anti-angiogenic effect for substantially the duration of treatment. Preferably, such a blood level will be maintained for at least about 20% of the time between doses, more preferably for at least about 30% of the time between doses more preferably for at least about 50% of the time between doses, most preferably for at least about 70% of the time between doses. Therapy is continued for a period of time from about 10 days to about 6 months, or as determined by one of skill in the art. Optionally, treatment will continue chronically for a period longer than six months for as long as is needed. The present invention reduces host toxicity, allows for longer term administration of the chemotherapeutic agent in diseases or pathological conditions requiring it, and does not sacrifice, and perhaps even improves, anti-tumor efficacy. Optionally, increased efficacy will permit the use of shorter durations of therapy for selected angiogenic dependent conditions.

The anti-angiogenic molecule is preferably administered in dosages and dose frequencies sufficient to substantially saturate the selected target receptor or ligand. Substantial saturation is saturation of at least about 50% of targeted receptors. A more preferred level of saturation is at least about 80%, and a most preferred level of saturation is about 100%. Optionally, the anti-angiogenic molecule is administered at a dose and frequency sufficiently short to maintain a blood level sufficient to saturate the targeted survival factor for at least about 50% of the time between doses, more preferably at least about 70% of the time and most preferably at least about 90% of the time interval between doses. Using the concentrations required to achieve receptor saturation or ligand neutralization in vitro, and by analysis of serum concentrations of anti-angiogenic molecule in vivo, both the appropriate dose and schedule can be determined readily by one of skill in the art.

A preferred embodiment of the present invention comprises the administration of the antibody IMC-1C11, a KDR receptor antagonist with a chemotherapeutic agent. A preferred dose of IMC-1C11, is an amount that is sufficient to adequately saturate the targeted receptors or ligand. In in vitro experiments, 50% saturation of VEGF receptors was obtained as an IMC-1C11 concentration of 0.2 µg/ml, and 100% at a concentration of 3 µg/ml. A preferred level of saturation is about at least 50%, a more preferred level is about at least 80%, and a most preferred level is about 100% saturation. For therapy, a preferred dose regimen of IMC-1C11 is from about 5 mg/m$^2$ to about 700 mg/m$^2$, more preferably from about 7.5 mg/m$^2$ to about 225 mg/m$^2$, administered about twice per week.

Another preferred embodiment of the invention combines IMC-1C11 in the doses described above with vinblastine, administered in a low dose regimen, at a dose from about 0.5 mg/m$^2$ to about 3 mg/m$^2$ from about every 3 days to about every 7 days. Optionally, a suitable chemotherapeutic agent other than vinblastine is administered in a dosage and frequency that is of substantially equivalent efficacy to vinblastine (in the combination) at a dose from about 0.5 mg/m$^2$ to about 3 mg/m$^2$ from about every 3 days to about every 7 days.

In other embodiments of the present invention, doses of an anti-angiogenic molecule in amounts and dosing frequencies sufficient to provide levels of receptor or ligand saturation equivalent to that of IMC-1C11 in the doses about are combined with a chemotherapeutic agent in a dose and frequency equivalent to that of vinblastine above, and therapy is carried out for as long as is needed. An equivalent dose is one that, in the combination, is substantially as effective in arresting or inhibiting the angiogenic dependent condition, while being substantially as effective in minimizing or preventing significant chemotherapy induced toxicity. In one preferred embodiment of the present invention, an equivalent dose of another chemotherapeutic agent is determined using data derived from an animal model, an example of which is included herein, utilizing a chemotherapy-resistant cell line so that any observed antitumor effect is due to an effect on the vascular endothelium. A preferred dose of vinblastine in a mouse is from about 1 mg/m$^2$ to about 2 mg/m$^2$ more preferably about 1.5 mg/m$^2$ administered every three days. The MTD of this drug in mice is approximately 4-5 times that of a human, and a preferred dose is $\frac{1}{16}$-$\frac{1}{20}$ of the MTD in mice. A preferred dose of DC101 in a mouse is about 800 µg administered intraperitoneally every three days. The use of DC101 and vinblastine showed a therapeutic effect upon neuroblastoma cell lines grown as xenografts in SCID mice. (L. Witte, L, et al., Monoclonal antibodies targeting the VEGF receptor-2 (flk1/KDR) as an anti-angiogenic therapeutic strategy. *Cancer Metastasis Rev.* 17:155-161. (1998); Prewitt, 1999). In yet another preferred embodiment of the present invention, low-dose vinblastine is administered every 3 days in combination with IMC-1C11 (p1C11).

The anti-angiogenic molecule and chemotherapeutic agent of the present invention are administered together or separately. Routes of administration include but are not limited to oral, sublingual, and parenteral, including intravenously, subcutaneously, transcutaneously, intraperitoneally, intrapleurally, and intrathecally. Optionally the molecule and agent are formulated into a pharmaceutical preparation for administration via the desired route. The agent and molecule are administered via the same route or via different routes In one aspect of the present invention, there is provided a kit comprising an anti-angiogenic molecule and a chemotherapeutic agent to be administered to a mammal in an amount effective to produce a regression or arrest of an angiogenic dependent condition while minimizing or preventing significant toxicity of the chemotherapeutic agent. Such a kit optionally comprises an anti-angiogenic molecule and a chemotherapeutic agent in one or more than one containers for administration at about the same time points or at different times. Optionally, the anti-angiogenic molecule is administered intermittently and the chemotherapeutic agent is administered continuously or in a manner that permits the maintenance of a suitable blood concentration. It is an aspect of the present invention that such treatment optionally is administered for a prolonged period or chronically, without substantial chemotherapy induced toxicity. Routes of administration include but are not limited to oral and parenteral, including but not limited to intravenous, subcutaneous, percutaneous, intrathecal and intraperitoneal. Patients that may be treated with the methods and compositions of the present invention include any patients with an angiogenic dependent disease.

The angiogenic dependent diseases encompassed by the scope of the present invention include, but are not limited to neoplasms, collagen vascular diseases or autoimmune diseases. All neoplasms are suitable for treatment with the present invention, however preferred neoplasms are solid tumors. More preferred are breast carcinoma, lung carcinoma, prostate carcinoma, colon carcinoma, prostate carcinoma, ovarian carcinoma, neuroblastoma, central nervous system tumor, neuroblastoma, glioblastoma multiforme or melanoma, and a preferred mammal to receive treatment is a human.

Antibodies used in this invention may be produced in a prokaryotic or eukaryotic cell. Techniques for the creation of and production of such antibodies, or portions thereof are well know in the field and are within the knowledge of one of ordinary skill in the art. Techniques used for preparation of monoclonal antibodies, include but are not limited to, the hybridoma technique (Kohler & Milstein, *Nature*, 256:495-497 (1975)), the trioma technique, the human B-cell hybridoma technique (Kozbor et al., *Immunology Today* 4:72, (1983)), and the EBV-hybridoma technique to produce human monoclonal antibodies (Cole, et al., 1985, In *Monoclonal Antibodies and Cancer Therapy*, Alan R. Liss, Inc., pp. 77-96).

DNA encoding chimerized antibodies may be prepared by recombining DNA substantially or exclusively encoding human constant regions and DNA encoding variable regions derived substantially or exclusively from the sequence of the variable region of a mammal other than a human. DNA encoding humanized antibodies may be prepared by recombining DNA encoding constant regions and variable regions, other than the CDRs, derived substantially or exclusively from the corresponding human antibody regions and DNA encoding CDRs derived substantially or exclusively from a mammal other than a human.

The DNA deletions and recombinations of the present invention may be carried out by known methods, such as those described in PCT applications WO 93/21319, WO 89/09622, European Patent applications 239,400, 338,745 and 332,424 and/or other standard recombinant DNA techniques. Conventional methods, such as those employed in the construction of vectors and plasmids, the insertion of genes encoding polypeptides into such vectors and plasmids, or the introduction of plasmids into host cells, are well known to those of ordinary skill in the art and are described in numerous publications including Sambrook, J., Fritsch, E. F. and Maniatis, T. (1989) *Molecular Cloning: A Laboratory Manual*, 2nd edition, Cold Spring Harbor Laboratory Press, and in Ausubel et al. (Eds) *Current Protocols in Molecular Biology*, Green Publishing Associates/Wiley-Interscience, New York (1990).

The invention also includes functional equivalents of the antibodies described in this specification. Functional equivalents have binding characteristics comparable to those of the antibodies, and include, for example, chimerized, humanized and single chain antibodies as well as fragments thereof. Methods of producing such functional equivalents are disclosed in PCT Application No. WO 93/21319, European Patent Application No. EPO 239,400; PCT Application WO 89/09622; European Patent Application No. EP338,745; and European Patent Application EPO 332,424.

The present invention also includes chimeric, single chain, and humanized antibodies, as well as Fab fragments, or the product of an Fab expression library. The antibodies of the invention can be prepared by conventional methods which are well know in the art.

Techniques described for the production of single chain antibodies (U.S. Pat. No. 4,946,778, incorporated herein by reference) are adapted to produce single chain antibodies to immunogenic polypeptide products of this invention.

According to another embodiment of the invention, the antibodies of the invention can be prepared by recombinant DNA techniques by cloning and expressing all or part of a known antibody. Using such techniques, which are known in the art, a chimeric or humanized version of non-human antibodies can be prepared. For example, a chimeric or humanized version of monoclonal antibody can be readily prepared by cloning the gene encoding this antibody in to an appropriate expression vector. Useful in this regard are the nucleic acids which encodes an amino acid sequence wherein the amino acid sequence comprises the variable region, hyper-variable region, or both of a monoclonal antibody that specifically binds to a vascular endothelial survival factor.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred embodiment of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pbs, pD10, phagescript, psiX174, pbluescript SK, pbsks, pNH8A, pNH16a, pNH18A, pNH46A (Stratagene); ptrc99a, pKK223-3, pKK233-3, pDR540, pRIT5 (Pharmacia). Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

The constructs in host cells are used in a conventional manner to produce the gene product encoded by the recombinant sequence. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989).

According to another aspect of the invention, transgenic mammals are provided that express humanized antibodies to immunogenic products of this invention. Novel transgenic mammalian hosts, other than primates, particularly other than human, are provided, where the host is capable of mounting an immune response to an immunogen, where the response produces antibodies having primate, particularly human, constant and/or variable regions or such other effector peptide sequences of interest.

The hosts are characterized by being capable of producing xenogenic or modified antibodies as a result of substitution and/or inactivation of the endogenous immunoglobulin subunit encoding loci. The modifications retain at least a portion of the constant region which provides for assembly of the variable region binding site bonded at the C-terminus to a functional peptide. The functional peptide takes many forms or conformations and serves, for example, as an enzyme, growth factor, binding protein, ligand, cytokine, effector protein, chelating proteins, etc. The antibodies are any isotype, i.e., IgA, IgD, IgE, IgG, IgM or subtypes within the isotype.

Transgenic hosts include murine, lagomorpha, ovine, porcine, equine, canine, feline, and the like. For the most part, mice have been used for the production of B-lymphocytes. It should be understood that other animals may be readily substituted for the mice, following the same procedures.

Humanized and chimeric antibodies are prepared according to the following strategies. In one strategy, the human heavy and light chain immunoglobulin gene complexes are introduced into the mouse germ line and in a separate step the corresponding mouse genes are rendered non-functional. Polynucleotides encoding human heavy and light chain are reconstructed in an appropriate eukaryotic or prokaryotic microorganism and the resulting polynucleotide fragments are then introduced into pronuclei of fertilized mouse oocytes or embryonic stem cells. Inactivation of the endogenous mouse immunoglobulin loci is achieved by targeted disruption of the appropriate loci by homologous recombination in mouse embryonic stem cells. In each case chimeric animals are generated which are derived in part from the modified embryonic stem cells and are capable of transmitting the genetic modifications through the germ line. The mating of mouse having a human immunoglobulin loci to mouse having an inactivated immunoglobulin loci yields animals that produce purely human antibody.

In another strategy, fragments of the human heavy and light chain immunoglobulin loci are used to directly replace the corresponding mouse loci by homologous recombination in mouse embryonic stem cells. This is followed by the generation of chimeric transgenic animals. The resulting human antibodies are isolated, for example, from other proteins by using an affinity column, having an Fc binding moiety, such as protein A, or the like.

The organization, relative location of exons encoding individual domains, and location of splice sites and transcriptional elements in a number of animals are known by those of ordinary skill in the art. In human, for example, the immunoglobulin heavy chain locus is located on chromosome 14. In the 5'-3' direction of transcription, the locus comprises a large cluster of variable region genes (VH), the diversity (D) region genes, followed by the joining (JH) region genes and the constant (CH) gene cluster. The size of the locus is estimated to be about 2,500 kilobases (kb). During B-cell development, discontinuous gene segments from the germ line Ig H locus are juxtaposed by means of a physical rearrangement of the DNA.

Production of a functional heavy chain immunoglobuline polypeptide requires three discontinuous DNA segments, from the VH, D, and JH regions, to be joined in a specific sequential fashion generating the functional units. Once these units are formed specific heavy chains are produced following transcription of the immunoglobuline locus. There are two loci for immunoglobuline light (Ig L) chains, the kappa locus on human chromosome 2 and the lambda locus on human chromosome 22. The structure of the Ig L loci is similar to that of the Ig H locus, except that the D region is not present.

The entire V region, or various fragments of the V region is used to produce a broad spectrum of high affinity antibodies. For example, a subset of the known V region genes of the human heavy and light chain Ig loci (Berman et al., EMBO J. 7: 727-738 (1988)) is used to produce transgenic hosts, which transgenic host are capable of mounting a strong immune response and provide high affinity antibodies.

Antibodies or antibody analog producing B-cells from the transgenic host are used, for example, for fusion to a mouse myeloid cell to produce hybridomas or immortalized by other conventional process, i.e., transfection with oncogenes. These immortalized cells are then grown, for example, in continuous culture or introduced into the peritoneum of a compatible host for production of ascites.

As discussed above, present invention also provides for the production of polyclonal human anti-serum or human monoclonal antibodies or antibody analogs provided they retain the activities of the antibodies of the invention. Epitope binding component of the present invention refers to proteins consisting of one or more polypeptides substantially encoded by genes of the immunoglobulin superfamily (i.e., The Immunoglobulin Gene Superfamily, Williams & Barclay In: Immunoglobulin Genes, Honjo, Alt, and Rabbitts, eds., (1989) incorporated herein by reference). For example, an epitope binding component comprises part or all of a heavy chain, part or all of a light chain, or both. However, an epitope binding component must contain a sufficient portion of an immunoglobulin superfamily gene product to retain the ability to bind to a specific target, or epitope.

Included within the scope of this invention is bispecific antibodies that are formed by joining two epitope binding components that have different binding specificities.

In general, modifications of the genes encoding the desired epitope binding components are readily accomplished by a variety of well-known techniques, such as site-directed mutagenesis (see, Gillman & Smith, Gene 8:81-97 (1979) and Roberts, et. al., Nature 328:731-734 (1987), both of which are incorporated herein by reference).

In preferred embodiments of the invention, the epitope binding component of the antibody of this invention is encoded by immunoglobulin genes that are "chimeric" or "humanized" (see, generally, Queen (1991) Nature 351:501, which is incorporated herein by reference). Once expressed, VE-cadherin antibodies, epitope binding components, their dimers, or individual light and heavy chains are purified according to standard procedures of the art, for example, ammonium sulfate precipitation, fraction column chromatography, gel electrophoresis and the like (see, generally, Scopes, Protein Purification, Springer-Verlag, N.Y. (1982)). Once purified, partially or to homogeneity as desired, the antibodies and fragments thereof are then used, for example, therapeutically, diagnostically, in drug screening techniques, or in developing and performing assay procedures, such as immunofluorescent staining, and the like.

The examples which follow are set forth to aid in understanding the invention, but are not intended to, and should not be construed as, limiting the scope of the invention in any manner.

EXAMPLES

Cells and culture conditions: Neuroblastoma cell lines SK-N-MC, SK-N-AS were obtained from American Type Culture Collection (ATCC) and expanded as a monolayer culture by serial passage on tissue culture plates (Nunc, Denmark) in DMEM, 5% fetal bovine serum (Gibco, Grand Island, N.Y., USA). Human umbilical vein endothelial cells (HUVEC) (Clonetics, San Diego, Calif.) were expanded on 1% gelatin-coated tissue culture plates in MCDB131 culture medium (JRH Biosciences, Lenexa, Kans., USA) supplemented with 5 ng/ml bFGF (R&D, Minneapolis, Minn.), 10 units/ml heparin (Wyeth-Ayerst Canada), 10 ng/ml EGF (UBI, Lake Placid, N.Y.) and 10% fetal bovine serum.

In vitro determination of drug sensitivity: Three thousand cells in 200 µl growth media per well were plated in 96-well flat bottom tissue culture plates (Nunc, Denmark) and incubated at 37° C., 5% $CO_2$ for 24 hours prior to initiation of treatment. The cells were then washed with PBS and treated with 1-500 ng/ml vinblastine sulphate (Calbiochem, La Jolla, Calif.) for 24 hours, in groups of eight wells per dose. The cells were then pulsed for 6 hrs with 2 µCi/well of methyl-$^3$H-thymidine (Amersham Life Science, Buckinghamshire, England). The plates were frozen, thawed and the DNA harvested onto a filtermat using a Titertek Cell Harvester. Incorporated radioactivity was measured on Wallac 1205 Beta-Plate Scintillation Counter (Wallac Oy, Finland) and proliferation was expressed as a percentage of $^3$H-thymidine in treated cells vs. that in controls.

In vivo tumor growth assessment: SK-N-MC, cells were harvested using 1% Trypsin EDTA (GibcoBRL, Gaithesburg, Md.), and single cell suspension of $2\times10^6$ cells in 0.2 ml of growth media was injected subcutaneously into the flanks of 4-6 week old CB-17 SCID mice (Charles River, St-Constant, Quebec). Approximately 3 weeks later, most tumors had grown to ~0.75 cm$^3$, and mice were randomized into groups of 5 animals. Two independent experiments were performed, each totaling 20 animals in 4 groups. The treatment was as follows:

Group I (Control)—0.4 ml of PBS (DC101 vehicle) i.p. every three days and 0.15 ml injectable saline (vinblastine vehicle) i.p. every three days.

Group II—0.4 ml of 2 mg/ml DC101 antibody (800 µg/mouse) (24) every three days and 0.15 ml of injectable saline i.p. every three days Group III—vinblastine sulfate 0.75 mg/m$^2$ i.p. bolus at the start of therapy, followed by 1 mg/m$^2$/day via subcutaneous Alzet osmotic pumps (Alza Corp, Palo Alto, Calif.) for 3 weeks, followed by maintenance therapy with 0.15 ml of 0.067 mg/ml vinblastine sulfate (1.5 mg/m$^2$) i.p. every three days, and 0.4 ml of PBS i.p. every three days Group IV—combination of DC101 and vinblastine at doses identical to the single agent groups.

The body weight, tumor size and general clinical status of the animals were recorded every 2-3 days. Perpendicular tumor diameters were measured using a vernier scale caliper and tumor volume was estimated using the formula for ellipsoid: (width$^2$×length)/2. Growth curves were statistically analyzed using repeated measures ANOVA. All animal care was in accordance with institutional guidelines. As required by institutional guidelines, the mice were sacrificed when tumor size reached 1.5 cm$^3$ or 7.5-10% of their body weight.

Histology: All tumors were excised, fixed in 10% (v/v) formalin and processed for immunohistochemical analysis. To obtain adequate tissue for the combination treatment group, two mice were sacrificed at 7.5 weeks of treatment. Paraffin blocks were cut to 5 µm sections and stained with haematoxylin/eosin for morphology evaluation and with Apoptosis Detection System (Promega, Madison, Wis.) for assessment of programmed cell death.

Relative tumor vascularity assessed by an FITC-Dextran perfusion assay: The method was designed to assess the relative functionality of the tumor vasculature. $2\times10^6$ SK-N-AS neuroblastoma cells were injected into the flanks of CB-17 SCID mice. Tumors were allowed to grow to approximately 0.75 cm$^3$ at which point tumor bearing mice were then treated with 1 mg/m$^2$ vinblastine i.p. every three days, 800 µg DC101 i.p. every three days, combination of the two agents or saline as a control. At 14 days, when divergence in tumor growth between the treatment groups was clearly evident, 0.2 ml of 25 mg/ml FITC-Dextran in PBS (Sigma, St. Louis, Mo.) was injected systemically into the lateral tail vein of each mouse and allowed to circulate for 20-30 minutes. Mice were then sacrificed by cervical dislocation and blood samples were collected into heparinized tubes by cardiac puncture for assessment of systemic fluorescein levels. Tumors were resected from the surrounding connective tissue being careful to avoid spillage of intra-vascular contents, weighed and placed into tubes containing 1:10 dispase (Collaborative Research, Two Oaks, Bedford, Mass.). To normalize for dilution caused by the difference in tumor sizes, 1 ml of 1:10 dispase was added per 0.5 g of tissue. Tumors were incubated in a dark 37° C. shaker overnight. The tissue was homogenized, centrifuged at 5000 rpm for 10 minutes, and the supernatant was collected and stored in the dark until further analysis. Blood samples were centrifuged immediately following collection, plasma separated and protected from light at 4° C. until analysis. Fluorescence readings were obtained on a FL600 Fluorescence Plate Reader (Bio-tek Instruments Inc., Winooski, Vt., USA), from a standard curve created by serial dilution of the FITC-dextran used for injection. The ratio of tumor fluorescence:plasma fluorescence was assumed to be reflective of the degree of tumor perfusion.

In vivo angiogenesis assessment by the Matrigel plug assay (5,25): Matrigel (Collaborative Biomedical Products, Bedford, Mass.) stored at −20° C., was thawed at 4° C. overnight and mixed with 500 ng/ml bFGF. 0.5 ml of this mixture was then injected subcutaneously into the shaved flanks of twenty 6-8 week old female Balb/cJ mice (Jackson Labs, Bar Harbor, Me.). Five mice, used as negative controls, were injected with Matrigel alone. Three days later, treatment mice were randomized into four groups as follows:

Group I—saline i.p.,
Group II—800 µg DC101 i.p.
Group III—1 mg/m$^2$ vinblastine i.p.
Group IV—combination therapy.

All 25 mice were treated on day 4 and 7 and sacrificed on day 10. Blood samples were collected into heparinized tubes by cardiac puncture, centrifuged immediately following their collection, plasma separated and protected from light at 4° C. The Matrigel plugs were resected from surrounding connective tissues, placed into tubes containing 1 ml of 1:10 dispase and incubated in the dark in a 37° C. shaker overnight. The following day, the plugs were homogenized, centrifuged at 5000 rpm for 10 minutes and supernatant saved in the dark for analysis of fluorescence. Fluorescence readings were obtained on FL600 Fluorescence Plate Reader using a standard curve created by serial dilution of FITC-dextran used for injection. Angiogenic response was expressed as a ratio of Matrigel plug fluorescence:plasma fluorescence.

In vitro determination of differential drug sensitivity: Prior to undertaking our in vivo experiments we established a dose of vinblastine, at which significant toxicity of endothelial, but not tumor, cells was observed. To do so, we optimized growth conditions to achieve comparable levels of mitotic activity in two human neuroblastoma cell lines (SK-NM-C and SK-N-AS) and HUVEC. All three cell lines were grown in DMEM with 10% bovine serum, but the HUVEC were grown on gelatinized plates and in the presence of additional growth factors (bFGF and EGF). The untreated controls show similar levels of $^3$H-Thymidine incorporation for all three cell lines thus eliminating the concern that the differences in proliferation may be inherent. At the higher concentrations of vinblastine used (e.g. 100-400 ng/ml) all three cell populations were strongly inhibited, especially HUVEC. In striking contrast, at the lowest concentrations (e.g. 0.78 ng/ml) vinblastine retained almost the same degree of inhibitory activity against HUVEC, whereas anti-proliferative activity against two tumor cell lines was not. The source of this differential sensitivity is not clear, but it should be noted that at least one of the tumor cell lines, SK-N-MC, is positive for multidrug resistance-associated protein (MRP). These in vitro findings suggest that the lowering of the usual maximum tolerated dose (MTD) used in the clinic may allow retention of good vinblastine activity against dividing endothelial cells present in tumors.

In vivo tumor growth assessment: Building on this in vitro difference in sensitivity to vinblastine, we went on to evaluate lower doses of vinblastine in an in vivo model, using an increased dose frequency to maximize the endothelial injury. Xenografts of either SK-N-MC neuroepithelioma or SK-N-AS neuroblastoma cell lines were implanted subcutaneously in the flanks of 4-6 week old. CB-17 SCID mice and grown to ~0.75 cm$^3$ before initiation of treatment. The first treatment group, treated with DC101, an anti-Flk1 receptor antibody shown previously to inhibit growth of different kinds of human xenografts in mice and in mouse tumor models (5), showed an anticipated effectiveness in inhibiting tumor growth, but, its effect was not sustained. The findings in the second treatment group (vinblastine alone), were even more surprising. This agent, traditionally thought to act by inhibiting tumor cell proliferation through inhibition of tubulin assembly, produced significant, albeit not sustained, regression of tumor growth even though used at subclinical low-dose. This growth delay in the vinblastine group was further potentiated with the simultaneous treatment with the anti-flk-1 antibody, DC101. The combination treatment induced an initial response comparable to the other treatment groups but then caused further, long term, tumor regression. To date, the mice in combination therapy group have not manifested any resistance to the treatment or recurrence of disease, despite almost seven months of continuous treatment. The mice remain healthy, with almost no evidence of tumor, except for a small, barely palpable remnant in one of the mice.

Toxicity evaluation: Anti-vascular therapy would be expected to show minimal toxicity in the post-natal stage of development. To evaluate this aspect of DC101/vinblastine combination therapy, the health status of the mice was monitored. Weight was plotted at regular intervals and considered a surrogate for evaluation of systemic well being, anorexia, or failure to thrive. No significant differences in weights were seen between the four groups. The weight curve of the DC101 group parallels very closely that of the control group. The vinblastine group showed some weight gain retardation, but the differences never became significantly different from controls. Similarly, the toxicity profile in the combination treatment group was very similar to those in the single agent groups, with the exception of a transient episode of weight loss associated with diarrhea. The episode lasted approximately 2-3 weeks and was unlikely to be due to the therapy as the mice recovered without interruption of treatment. Other usual signs of drug toxicity in mice such as ruffled fur, anorexia, cachexia, skin tenting (due to dehydration), skin ulcerations or toxic deaths, were not seen at the doses used in our experiments. Diarrhea, a common sign of vinblastine toxicity when doses of 10 mg/m$^2$ are used, was generally not observed, except for the above mentioned episode.

Histopathologic analysis: To further elucidate the mechanisms involved in the tumor regression following treatment with vinblastine, DC101, or the combined therapy, tissue histopathology assessment was undertaken. Cancer cells with high nuclear to cytoplasmic ratio form cuffs around central vessels, and apoptotic cells characterized by pyknotic nuclei and cytoplasmic blebbing, are only evident as a thin rim at the periphery of the cuffs. The nuclei of these cells stain strongly for terminal deoxynucleotidyl transferase (TUNEL) reactivity, as expected for cells undergoing apoptosis. Vinblastine alone or DC101 treatment alone both show an increase in the width of the apoptotic rims, suggesting the cells most distal to the tumor vasculature are primarily affected, but a large percentage of viable tumor cells still survive in the center of the cuff. In contrast, histology of the combined therapy group, as would be predicted by the regression in tumor size in this treatment group at the time of analysis, shows overwhelming loss of both cell viability and pre-existing tumor architecture. There is a close similarity of the appearance of H/E and TUNEL stain. Interestingly, we observed signs of endothelial cell toxicity in all of the treatment groups. Rather than a typical single layer of flattened endothelial cells surrounding the vascular lumen in untreated group, we observed edema, and detachment from surrounding basement membrane and leading to complete vascular wall disintegration and tumor cell death.

Tumor perfusion by assessment of intravascular fluorescence: To further explore the possibility that tumor regression induced with treatment using DC101 and vinblastine was indeed due to the vascular injury, rather than a direct anti-tumor cell effect, we assessed tumor perfusion directly by using a FITC-Dextran fluorescence method. Mice carrying established subcutaneous SK-N-AS human neuroblastoma xenografts (~0.75 cm$^3$) were randomized into four groups and treated systemically with either saline control, DC101, vinblastine or combination therapy for 10 days. FITC-Dextran was injected into the lateral tail vein and equilibrated throughout the vascular compartment. The majority of the blood-borne dextran, because of its 150 kDa size, remains intravascular, and despite some perivascular losses due to changes in vascular permeability and the possibility of interstitial hemorrhages, the fluorescence is reflective of the overall volume of blood passing through the tumor vasculature. Since our therapy is chronic in its nature, changes in intratumoral vascular/blood volume are likely to represent structural changes rather than transient fluxes in vascular permeability. By these criteria DC101 alone caused a 47% decrease in tumor perfusion, whereas vinblastine alone resulted in a 41% decrease, and the combination of the two drugs resulted in 65% perfusion inhibition. Of interest is the appreciable difference in gross vascularity in the corresponding tumor specimens.

Effects of chemotherapy treatments on in vivo angiogenesis: The direct assessment of tumor vasculature does not provide any clues as to whether the apparent vascular inhibition within the tumor is a primary cause or a secondary consequence of the tumor regression. Evidence for the former would provide support for the hypothesis that low-dose vinblastine treatment alone is potentially anti-angiogenic, and the extent of this anti-angiogenic effect may be further enhanced by concurrent treatment with DC101. Again, the ratio between intra- and extra-vascular volume within the tumor could be also somewhat affected by transient changes in vascular permeability. To address these questions, we repeated the same fluorescence measurement using an in vivo Matrigel plug angiogenesis assay. Four treatment groups were treated with an identical therapeutic regimen as in the tumor perfusion experiment. The regression of vascularity in subcutaneously implanted Matrigel pellets was quantitatively assessed by measuring the fluorescence of circulating FITC-labeled dextran. DC101 administration inhibited bFGF induced vascularization to 50% of the positive control group, and vinblastine administration inhibited vascularization to 62.5% of the positive control group. There was again an enhanced effect with combination therapy, which reduced the Matrigel pellet fluorescence, and by inference vascularization to 29.2% of control, a level only marginally different to the negative control (Matrigel not supplemented with growth factors).

Thus, large (0.75 cm$^3$) established human neuroblastoma xenografts could be induced to completely regress with this combination strategy, whereas either agent alone caused only partial and temporary regressions with relapses observed in all animals treated at between 30-50 days after initiation of the individual therapy treatments. In striking contrast, a fully regressed state could be induced and maintained for as long as the combination therapy was maintained, which in our case was 200 days, in the absence of any significant toxicity, as assessed by lack of weight loss. Thus, synergistic inhibition was obtained by the combination treatment. No myelosuppression has been observed.

The dose of vinblastine used in our experiments was in the range of 1.5 mg/m$^2$, every 3 days, which is approximately 3 times the MTD of this drug in humans, and $\frac{1}{16}$-$\frac{1}{20}$ of the MTD in mice, given the fact that the MTD of vinblastine in mice is 4-5 times higher than in humans. Using the Matrigel plug assay, we demonstrated that continuous low dose vinblastine administration can cause a direct anti-angiogenic effect in vivo. The combined effect with DC101 was significant.

What is claimed is:

1. A method of treating a solid tumor in a human patient by inhibiting angiogenesis, comprising:

administering to the human patient comprising a solid tumor selected from the group consisting of breast carcinoma, lung carcinoma, prostate carcinoma, colon carcinoma, ovarian carcinoma, neuroblastoma, central nervous system tumor, glioblastoma multiforme and melanoma:

(a) an antibody or binding fragment thereof that (i) specifically binds to a flk-1/KDR receptor and (ii) inhibits angiogenesis; and (b) a chemotherapeutic agent having anti-angiogenic activity selected from the group consisting of vincristine, vinblastine, vinorelbine, vindesine, paclitaxel, docetaxel, 5 FU, cisplatin, carboplatin, irinotecan, topotecan and cyclophosphamide, in amounts and frequencies effective, in combination, to inhibit formation of blood vessels supplying the solid tumor while minimizing or preventing toxicity of the chemotherapeutic agent, wherein the chemotherapeutic agent is administered at a dose intensity of less than about 10% of the dose intensity of the chemotherapeutic agent when used in a conventional chemotherapeutic regimen, wherein said administering is continued over a period of time from about 10 days to about 6 months, and wherein synergistic tumor inhibition is obtained.

2. The method of claim 1, wherein:

the chemotherapeutic agent is selected from the group consisting of vincristine, vinblastine, vinorelbine, and vindesine;

the solid tumor is selected from the group consisting of neuroblastoma and neuroepithelioma; and said administering is continued for a period of about 6 months.

3. The method of claim 2, wherein the chemotherapeutic agent is vinblastine.

4. The method of claim 1, wherein:

said administering is continued for a period of about 6 months.

5. The method of claim 4, wherein the chemotherapeutic agent is vinblastine.

* * * * *

SEQUENCE LISTING

```
<160> NUMBER OF SEQ ID NOS: 16

<210> SEQ ID NO 1
<211> LENGTH: 10
<212> TYPE: PRT
<213> ORGANISM: Mouse

<400> SEQUENCE: 1

Gly Phe Asn Ile Lys Asp Phe Tyr Met His
1               5                   10

<210> SEQ ID NO 2
<211> LENGTH: 17
<212> TYPE: PRT
<213> ORGANISM: Mouse

<400> SEQUENCE: 2

Trp Ile Asp Pro Glu Asn Gly Asp Ser Asp Tyr Ala Pro Lys Phe Gln
1               5                   10                  15

Gly

<210> SEQ ID NO 3
<211> LENGTH: 8
<212> TYPE: PRT
<213> ORGANISM: Mouse

<400> SEQUENCE: 3

Tyr Tyr Gly Asp Tyr Glu Gly Tyr
1               5

<210> SEQ ID NO 4
<211> LENGTH: 10
<212> TYPE: PRT
<213> ORGANISM: Mouse

<400> SEQUENCE: 4

Ser Ala Ser Ser Ser Val Ser Tyr Met His
```

-continued

```
                1               5                    10
```

<210> SEQ ID NO 5
<211> LENGTH: 7
<212> TYPE: PRT
<213> ORGANISM: Mouse

<400> SEQUENCE: 5

```
Ser Thr Ser Asn Leu Ala Ser
 1               5
```

<210> SEQ ID NO 6
<211> LENGTH: 9
<212> TYPE: PRT
<213> ORGANISM: Mouse

<400> SEQUENCE: 6

```
Gln Gln Arg Ser Ser Tyr Pro Phe Thr
 1               5
```

<210> SEQ ID NO 7
<211> LENGTH: 117
<212> TYPE: PRT
<213> ORGANISM: Mouse

<400> SEQUENCE: 7

```
Gln Val Lys Leu Gln Gln Ser Gly Ala Glu Leu Val Gly Ser Gly Ala
 1               5                   10                  15

Ser Val Lys Leu Ser Cys Thr Thr Ser Gly Phe Asn Ile Lys Asp Phe
                20                  25                  30

Tyr Met His Trp Val Lys Gln Arg Pro Glu Gln Gly Leu Glu Trp Ile
            35                  40                  45

Gly Trp Ile Asp Pro Glu Asn Gly Asp Ser Asp Tyr Ala Pro Lys Phe
        50                  55                  60

Gln Gly Lys Ala Thr Met Thr Ala Asp Ser Ser Asn Thr Ala Tyr
 65                  70                  75                  80

Leu Gln Leu Ser Ser Leu Thr Ser Glu Asp Thr Ala Val Tyr Tyr Cys
                85                  90                  95

Asn Ala Tyr Tyr Gly Asp Tyr Glu Gly Tyr Trp Gly Gln Gly Thr Thr
            100                 105                 110

Val Thr Val Ser Ser
        115
```

<210> SEQ ID NO 8
<211> LENGTH: 108
<212> TYPE: PRT
<213> ORGANISM: Mouse

<400> SEQUENCE: 8

```
Asp Ile Glu Leu Thr Gln Ser Pro Ala Ile Met Ser Ala Ser Pro Gly
 1               5                   10                  15

Glu Lys Val Thr Ile Thr Cys Ser Ala Ser Ser Ser Val Ser Tyr Met
                20                  25                  30

His Trp Phe Gln Gln Lys Pro Gly Thr Ser Pro Lys Leu Trp Ile Tyr
            35                  40                  45

Ser Thr Ser Asn Leu Ala Ser Gly Val Pro Ala Arg Phe Ser Gly Ser
        50                  55                  60

Gly Ser Gly Thr Ser Tyr Ser Leu Thr Ile Ser Arg Met Glu Ala Glu
 65                  70                  75                  80
```

```
Asp Ala Ala Thr Tyr Tyr Cys Gln Gln Arg Ser Ser Tyr Pro Phe Thr
             85                  90                  95

Phe Gly Ser Gly Thr Lys Leu Glu Ile Lys Arg Ala
            100                 105
```

<210> SEQ ID NO 9
<211> LENGTH: 30
<212> TYPE: DNA
<213> ORGANISM: Mouse

<400> SEQUENCE: 9
ggcttcaaca ttaaagactt ctatatgcac                                      30

<210> SEQ ID NO 10
<211> LENGTH: 51
<212> TYPE: DNA
<213> ORGANISM: Mouse

<400> SEQUENCE: 10
tggattgatc ctgagaatgg tgattctgat tatgccccga agttccaggg c              51

<210> SEQ ID NO 11
<211> LENGTH: 24
<212> TYPE: DNA
<213> ORGANISM: Mouse

<400> SEQUENCE: 11
tactatggtg actacgaagg ctac                                            24

<210> SEQ ID NO 12
<211> LENGTH: 30
<212> TYPE: DNA
<213> ORGANISM: Mouse

<400> SEQUENCE: 12
agtgccagct caagtgtaag ttacatgcac                                      30

<210> SEQ ID NO 13
<211> LENGTH: 21
<212> TYPE: DNA
<213> ORGANISM: Mouse

<400> SEQUENCE: 13
agcacatcca acctggcttc t                                               21

<210> SEQ ID NO 14
<211> LENGTH: 27
<212> TYPE: DNA
<213> ORGANISM: Mouse

<400> SEQUENCE: 14
cagcaaagga gtagttaccc attcacg                                         27

<210> SEQ ID NO 15
<211> LENGTH: 351
<212> TYPE: DNA
<213> ORGANISM: Mouse

<400> SEQUENCE: 15
caggtcaagc tgcagcagtc tggggcagag cttgtggggt caggggcctc agtcaaattg     60
tcctgcacaa cttctggctt caacattaaa gacttctata tgcactgggt gaagcagagg    120
cctgaacagg gcctggagtg gattggatgg attgatcctg agaatggtga ttctgattat    180

```
gccccgaagt tccagggcaa ggccaccatg actgcagact catcctccaa cacagcctac    240
ctgcagctca gcagcctgac atctgaggac actgccgtct attactgtaa tgcatactat    300
ggtgactacg aaggctactg gggccaaggg accacggtca ccgtctcctc a             351

<210> SEQ ID NO 16
<211> LENGTH: 324
<212> TYPE: DNA
<213> ORGANISM: Mouse

<400> SEQUENCE: 16
gacatcgagc tcactcagtc tccagcaatc atgtctgcat ctccagggga gaaggtcacc     60
ataacctgca gtgccagctc aagtgtaagt tacatgcact ggttccagca gaagccaggc    120
acttctccca aactctggat ttatagcaca tccaacctgg cttctggagt ccctgctcgc    180
ttcagtggca gtggatctgg gacctcttac tctctcacaa tcagccgaat ggaggctgaa    240
gatgctgcca cttattactg ccagcaaagg agtagttacc cattcacgtt cggctcgggg    300
accaagctgg aaataaaacg ggcg                                           324
```